United States Patent [19]

Miyashita

[11] Patent Number: 5,320,784

[45] Date of Patent: Jun. 14, 1994

[54] CRYSTAL COMPRISING AN INDOLINOSPIROBENZOTHIOPYRAN DERIVATIVE AND ITS RING OPENED ISOMER

[75] Inventor: Akira Miyashita, Ageo, Japan

[73] Assignee: Otsuka Kagaku Kabushiki Kaisha, Osaka, Japan

[21] Appl. No.: 938,045

[22] PCT Filed: Mar. 11, 1992

[86] PCT No.: PCT/JP92/00294

§ 371 Date: Nov. 12, 1992

§ 102(e) Date: Nov. 12, 1992

[87] PCT Pub. No.: WO92/16531

PCT Pub. Date: Oct. 1, 1992

[30] Foreign Application Priority Data

Mar. 13, 1991 [JP] Japan .................... 3-47201

[51] Int. Cl.$^5$ .................... G02B 5/23; G02F 1/00
[52] U.S. Cl. .................... 252/583; 204/157.7; 252/586; 252/588; 252/589; 252/600; 430/78
[58] Field of Search ............ 252/583, 586, 588, 589, 252/600; 204/157.7; 548/407; 430/78

[56] References Cited

U.S. PATENT DOCUMENTS

| | | | |
|---|---|---|---|
| 3,407,145 | 10/1968 | Brule | 252/586 |
| 3,510,308 | 5/1970 | Foris et al. | 252/586 X |
| 3,631,172 | 12/1971 | Gautron | 252/586 X |
| 3,660,086 | 5/1972 | Tamai et al. | 252/586 X |
| 4,122,089 | 10/1978 | Kimura et al. | 548/407 X |
| 4,139,274 | 2/1979 | Yamashita et al. | 252/408.1 X |
| 4,565,779 | 1/1986 | Arakawa et al. | 548/407 X |
| 4,909,963 | 3/1990 | Kwak et al. | 252/586 |

Primary Examiner—Richard D. Lovering
Attorney, Agent, or Firm—Armstrong, Westerman, Hattori, McLeland & Naughton

[57] ABSTRACT

The object of this invention is to provide a novel compound suited for use as a piezochromic material.

This invention relates to a crystal comprising an indolinospirobenzothiopyran derivative of the following general formula and its ring opened isomer.

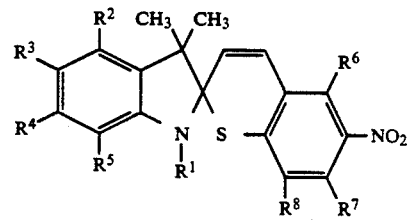

wherein $R^1$ stands for $C_{1-20}$ alkyl, aralkyl, methacryloxymethyl or a methacryloxyethyl; $R^2$, $R^3$, $R^4$, $R^5$, $R^6$ and $R^7$ may for example be hydrogen; $R^8$ may for example be hydrogen or methacryloxymethyl.

The invention further relates to a process for producing the crystal.

5 Claims, 2 Drawing Sheets

CRYSTAL COMPRISING AN INDOLINOSPIROBENZOTHIOPYRAN DERIVATIVE AND ITS RING OPENED ISOMER

TECHNICAL FIELD

The present invention relates to a crystal comprising an indolinospirobenzopyran derivative and its ring opened isomer, a process for producing the same and a piezochromic material comprising said crystal.

BACKGROUND ART

The organic compounds undergoing a reversible change of color on exposure to photic or thermal energy which are typical and best known are spiropyran derivatives and G. H. Brown: Photochromism (John Wiley & Sons, Inc., 1971), for one, can be consulted for a specific listing of such derivatives and their physical properties. However, when an attempt is made to exploit the hitherto-known spiropyran derivatives commercially in recording materials, they are found to have serious disadvantages. Thus, because the meta-stable species (ring opened isomers) are lacking in thermal stability in solutions as well as in polymeric binders, they tend to promptly revert to the ground state or fade out so that the chromic response at a necessary level cannot be sustained for a sufficient duration.

Meanwhile, as piezochromic compounds, there are known, inter alia, 9-(p-nitrophenylphenylmethylene)xanthene [J. Am. Chem. Soc., 79, 6020 (1957)], diflavine [J. Am. Chem. Soc., 80, 6312 (1958)], dehydrodianthrone [Chem. Ber., 100, 280 (1967), hexaphenylbiimidazolyl (Bull. Chem. Soc. Japan, 38, 685 (1965); ibid. 38, 2202 (1965); ibid, 43, 429 (1970)], tetraphenylvinyl dimer [Bull. Chem. Soc. Japan, 43, 1431 (1970)], phthalocyanine-cobalt complex [Journal of Synthetic Organic Chemistry, Japan, 30, 521 (1972)] and hydroxycarboxylic acid derivatives [Japanese Kokai Patent Publication No. 132857/1988], as well as spiropyranthiopyrans [Japanese Kokai Patent Publication No. 46079/1977] and spirobenzopyranoxadiazoline derivatives [Japanese Kokai Patent Publication No. 42880/1977], both of which are commonly referred to briefly as spiropyrans. However, many of these known compounds have several problems that must be overcome, viz. some require a substantial pressure for coloration or have only a low contrast of color between the colorless state and the colored state, while others are too labile, as very compounds, to be utilized as industrial materials and still others involve a complicated route for synthesis.

It is an object of the present invention to provide a piezochromic compound which insures a sufficient color density in a stable manner.

It is a further object of the invention to provide a piezochromic compound which can be intensely colored with a relatively low pressure to give a large contrast of color between the colored and colorless states and is superior in thermal stability.

It is a still further object of the invention to provide an expedient process for synthesizing such a piezochromic compound.

DISCLOSURE OF THE INVENTION

The inventor of the present invention explored in earnest for a spiropyran derivative free from the aforementioned disadvantages and insuring a stable or fatigueless piezochromic response and succeeded in isolating such a color-fast spiropyran derivative in the crystalline form. The inventor further found that this crystal changes color on application of a relatively small pressure and ultimately perfected the present invention.

The present invention relates to a crystal comprising an indolinospirobenzothiopyran compound of the following general formula and its ring opened isomer, a process for producing the same, and a piezochromic material comprising said crystal.

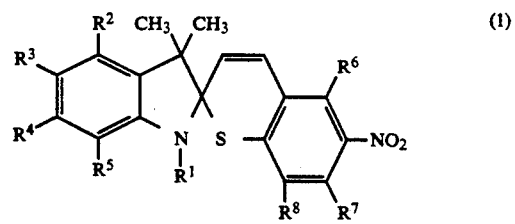

wherein $R^1$ means an alkyl group of 1 to 20 carbon atoms, an aralkyl group, a methacryloxymethyl group or a methacryloxyethyl group. $R^2$, $R^3$, $R^4$ and $R^5$ may be the same or different and each means a hydrogen atom, an alkyl group of 1 to 6 carbon atoms, an aryl group, an aralkyl group, an alkoxy group of 1 to 5 carbon atoms, a halogen atom, a cyano group or a nitro group. $R^6$ and $R^7$ may be the same or different and each means a hydrogen atom, an alkyl group of 1 to 6 carbon atoms, an aryl group, an aralkyl group, a halogen atom, a cyano group or a nitro group. $R^8$ means a hydrogen atom, an alkyl group of 1 to 6 carbon atoms, an alkoxy group of 1 to 5 carbon atoms, a chloromethyl group, a methacryloxymethyl group or a vinyl group.

As used in this specification, the term aryl group means, inter alia, phenyl and naphtyl, which may be substituted by $C_{1-6}$ alkyl, halogen or $C_{1-5}$ alkoxy. The aralkyl group includes, inter alia, benzyl, phenylethyl, naphtylmethyl, etc., the aromatic ring of which may be substituted by $C_{1-6}$ alkyl, halogen or $C_{1-5}$ alkoxy.

The crystal of the present invention can be obtained by dissolving a compound of general formula (1) in a low-polarity organic solvent, irradiating the resulting solution with ultraviolet light to cause the photoreaction product to crystallize out.

The inventor knows of only one report claiming that when an indolinospirobenzopyran derivative was irradiated with ultraviolet light in methylcyclohexane, there was obtained a pseudo-crystal having properties different from those of the original compound [J. Phys. Chem., 82, 2469 (1978)]. However, the compound used there is chemically different from the indolinospirobenzothiopyran of the present invention and, moreover, the above report presents no factual information or discussion about the piezochromism of the product.

The compound of general formula (1) which is used for producing the crystal of the invention can be produced by condensing a 2,3,3-trimethylindolenium iodide of the general formula

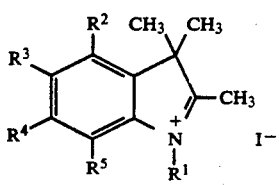

(2)

wherein $R^1$, $R^2$, $R^3$, $R^4$ and $R^5$ are as defined hereinbefore with a 5-nitrothiosalicylaldehyde derivative of the general formula

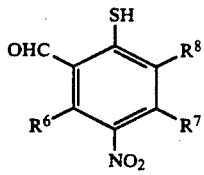

(3)

wherein $R^6$, $R^7$ and $R^8$ are as defined hereinbefore in the presence of a base such as an amine.

The compound of general formula (1) according to the present invention can also be produced by converting a 2,3,3-trimethylindolenium iodide of general formula (2) to a 2-methylene-3,3-dimethylindolenine derivative of the general formula

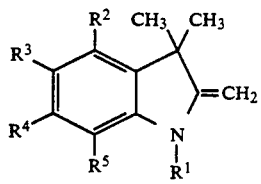

(4)

wherein $R^1$, $R^2$, $R^3$, $R^4$ and $R^5$ are as defined hereinbefore, which conversion can be easily achieved by treatment with a base such as an alkali metal hydroxide, and reacting this compound (4) with said 5-nitrothiosalicylaldehyde derivative of general formula (3) under heating.

Regarding the above 2,3,3-trimethylindolenium iodide, some species are the known compounds described in Helv. Chim. Acta, 23, 2471 (1940), Japanese Patent Publication No. 58654/1983, Japanese Kokai Patent Publication No. 232461/1987, Japanese Patent Publication No. 21780/1987 and Japanese Kokai Patent Publication No. 267783/1988, for instance, while others are compounds which can be easily prepared in accordance with the processes described in the above literature.

The starting 5-nitrothiosalicylaldehyde derivative of general formula (3) can be prepared typically by reacting a salicylaldehyde derivative of the general formula

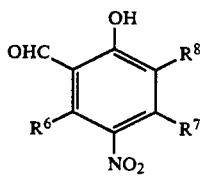

(5)

wherein $R^6$, $R^7$ and $R^8$ are as defined hereinbefore with N,N-dimethylthiocarbamoyl chloride, for example in the same manner as described in Japanese Kokai Patent Publication No. 54388/1985, to give a 2-O-(N,N-dimethylthiocarbamoyl)benzaldehyde derivative of the general formula

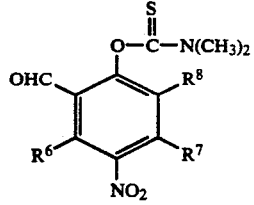

(6)

wherein $R^6$, $R^7$ and $R^8$ are as defined hereinbefore, then heating the same to isomerize to a 2-S-(N,N-dimethylthiocarbamoyl)benzaldehyde derivative of the general formula

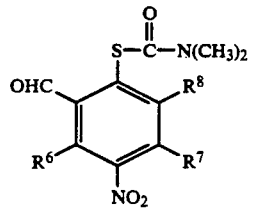

(7)

wherein $R^6$, $R^7$ and $R^8$ are as defined hereinbefore, and subjecting the same (7) to alkali hydrolysis.

The low-polarity organic solvent for use in the procedure of dissolving a compound of general formula (1) in an organic solvent and irradiating the same with ultraviolet light is preferably a nonpolar solvent. The nonpolar solvent for this purpose is not limited in kind only if it is able to dissolve the compound (1) and allow the photoreaction product to crystallize out. As preferred species, there may be reckoned various saturated hydrocarbons such as pentane, hexane, cyclohexane, methylcyclohexane, heptane, octane, nonane, decane, etc. and unsaturated hydrocarbons such as pentene, hexene, hexadiene, cyclohexene, cyclohexadiene, methylcyclohexene, heptene, heptadiene, benzene, toluene, xylene and so on.

The concentration of the compound of general formula (1) in the above solvent need only be high enough to allow the photoreaction product to neatly separate out as crystals. Generally speaking, the range of 0.001 mol/l ~ saturation concentration is preferred.

In the present invention, the compound of general formula (1) is exposed to ultraviolet radiation. The UV light source may be a household fluorescent lamp, a low-pressure mercury vapor lamp, a high-pressure mercury vapor lamp, a super high-pressure mercury vapor lamp or, for that matter, any light source giving an ultraviolet light output, although a super-high-pressure mercury vapor lamp fitted with a band pass filter adapted to transmit an UV emission of the wavelength of about 350 nm is preferably employed.

The concentration of the reaction mixture to be thus irradiated with ultraviolet light is not critical only if the photoreaction product may separate out with efficiency, although it may generally be in the range of about 0° C. to about 25° C.

The crystal of the invention, thus produced, can be easily separated from the reaction mixture by such known procedures as filtration and centrifugation.

The crystal of the invention, thus obtained, is a microfine crystal which is usually in the red series and composed of 30 to 60 mol % of the compound of general formula (1) and 70 to 40 mol % of its ring opened isomer. However, under a comparatively moderate pressure, the crystal instantly assumes a blue series color with good contrast. Moreover, the microfine crystal before and after the color change are both highly stable against heat.

Furthermore, the compound which has once assumed a blue series color gives, on dissolution in a solvent, a solution having a blue to blue-green color but when it is heated or exposed to light of the visible spectrum, gives a light yellow-colored clear solution of compound (1). And the cycle of such color change from yellow to red to blue may occur repeatedly.

The application of the crystal of the present invention in the field of piezochromic materials is now described.

The piezochromic material of the present invention can be manufactured by coating an appropriate medium with the crystal of the invention. The medium may be, for example, paper, plastic film, a board, a fabric or the like. In coating such a medium with the crystal particles of the invention, they may be uniformly dispersed in a resin powder or mineral powder, such as powdery silica gel or clay, which is inert to the crystals beforehand and after coating the medium with the dispersion, immobilized with a binder such as collodion.

Since the crystal of the invention has the function to change color on application of pressure as mentioned above, it can be utilized in pressure-sensitive recording materials, instant-developing color couplers, copying materials, toys, pressure measuring devices and nonlinear optical devices.

Furthermore, the crystal of the present invention can be easily reconverted to the initial spiropyran compound of general formula (1) by dissolving it in an organic solvent (e.g benzene, acetone, chloroform, methanol, etc.) or heating it to a temperature over its melting point. Therefore, by exploiting the above piezochromic function provided by the invention in combination with the photo- and thermochromism which is inherent in indolinobenzospirothiopyran compounds, it is possible to construct more sophisticated multi-functional recording materials.

The following advantages could be brought into existence by the present invention.

(1) The invention achieved a successful fixation of the ring opened isomer of an indolinospirobenzothiopyran compound which is otherwise labile and ready to fade out.

(2) The crystal with its ring opened form so fixed is stable against light but can be caused to change color with good contrast even with a minimal pressure which is by far lower than the pressure required for color change of the conventional piezochromic compounds (tens to thousands of $kg/cm^2$).

(3) The compound which has once undergone color change can be re-dissolved in a solvent and reused a number of times.

BEST MODE FOR CARRYING OUT THE INVENTION

The following examples are intended to illustrate the present invention in further detail.

EXAMPLE 1

A mixture of 12.0 g of 5-nitrosalicylaldehyde and 100 ml of chloromethyl methyl ether was cooled on an ice-bath and 43.9 g of anhydrous aluminum chloride was added in small portions. The mixture was stirred at room temperature for 10 minutes and, then, refluxed for 22 hours. This reaction mixture was cooled on an ice-bath and 200 ml of water was added with vigorous stirring, whereupon white crystals separated out. These white crystals are collected, dissolved in hot hexane and filtered and the mother liquor was cooled to give 14.9 g of 3-chloromethyl-5-nitrosalicylaldehyde as colorless needles (Yield 72%).

$^1$H-NMR (CDCl$_3$): δppm 4.72 (s, 2H, —CH$_2$Cl), 8.56 (s, 2H, ArH), 10.00 (s, 1H, CHO), 12.10 (s, 1H, OH)

EXAMPLE 2

In 100 ml of toluene was dissolved 10.5 g of 3-chloromethyl-5-nitrosalicylaldehyde followed by addition of 11.4 g of silver methacrylate. This mixture was heated at 120° C. for 2.5 hours and, then, cooled to room temperature. The resulting precipitate was filtered off and the toluene solution was concentrated under reduced pressure to give 12.7 g of 3-methacryloxymethyl-5-nitrosalicylaldehyde as light yellow powder (Yield 98%).

$^1$H-NMR (CDCl$_3$): δppm 2.00 (t, 3H, CH$_3$), 5.34 (s, 2H, —CH$_2$—), 5.67 (t, 1H, vinyl), 6.22 (m, 1H, vinyl), 8.53 (m, 2H, ArH), 10.00 (s, 1H, CHO)

EXAMPLE 3

In 300 ml of dimethylformamide were dissolved 13.8 g of 3-methacryloxymethyl-5-nitrosalicylaldehyde and 11.2 g of 1,4-diazabicyclo[2.2.2]octane and the solution was heated at 50° C. To this solution was added a solution of 12.9 g of N,N-dimethylthiocarbamoyl chloride in 50 ml of dimethylformamide gradually and the mixture was then heated at 50° C. for 2 hours. The reaction mixture was then diluted with 80 ml of water and extracted with ethyl acetate. The extract was washed with saturated aqueous sodium chloride solution and concentrated under reduced pressure to give 17.6 g of 2-O-(N,N-dimethylthiocarbamoyl)-3-methacryloxymethyl-5-nitrobenzaldehyde (Crude yield 96%).

$^1$H-NMR (CDCl$_3$): δppm 2.0 (m, 3H, CH$_2$), 3.5 (d, 6H, N—CH$_3$), 5.3 (d, 2H, —CH$_2$—), 5.7 (m, 1H, vinyl), 6.2 (m, 1H, vinyl), 8.6 (d, 1H, ArH), 8.7 (d, 1H, ArH), 10.0 (s, 1H, CHO)

EXAMPLE 4

A mixture of 12.6 g of 2-O-(N,N-dimethylthiocarbamoyl)-3-methacryloxymethyl-5-nitrobenzaldehyde and 100 ml of ethanol was refluxed for 21 hours. The reaction mixture was then concentrated under reduced pressure and the residue was dried in vacuo to give 10.7 g of 2-S-(N,N-dimethylthiocarbamoyl)-3-methacryloxymethyl-5-nitrobenzaldehyde (Yield 85%).

$^1$H-NMR (CDCl$_3$): δppm 2.0 (s, 3H, CH$_3$), 3.1 (d, 6H, N—CH$_3$), 5.5 (d, 2H, —CH$_2$—), 5.7 (m, 1H, vinyl), 6.2 (m, 1H, vinyl), 8.6 (d, 1H, ArH), 8.7 (d, 1H, ArH), 10.3 (s, 1H, CHO)

IR (KBr): 1720, 1690, 1660, 1535, 1345 cm$^{-1}$

EXAMPLE 5

To a mixture of 14.1 g of 2-S-(N,N-dimethylthiocarbamoyl)-3-methacryloxymethyl-5-nitrobenzaldehyde and 200 ml of methanol was added 140 ml of 0.64N aqueous sodium hydroxide solution at room temperature. To this reaction mixture, 380 ml of 0.49N hydrochloric acid was added to adjust it to pH 2 and the mixture was then concentrated under reduced pressure. The residue was extracted with ether and the extract was washed with water and concentrated under reduced pressure to give 9.79 g of 3-methacryloxymethyl-5-nitrothiobenzaldehyde as orange-colored crystals (Yield 87%).

$^1$H-NMR (CDCl$_3$): δppm 2.0 (m, 3H, CH$_3$), 5.3 (s, 2H, —CH$_2$—), 5.7 (m, 1H, vinyl), 6.2 (m, 1H, vinyl), 8.4 (m, 2H, ArH), 10.1 (s, 1H, CHO)

EXAMPLE 6

To a solution of 16.0 g of 2,3,3-trimethylindolenine in 100 ml of chloroform was added 15.9 g of methyl iodide and the mixture was heated in an autoclave at 80° C. for 21 hours. The resulting precipitate was collected by filtration to give 27.5 g of 1,2,3,3-tetramethylindolenium iodide as white crystals. To the crystals was added 270 ml of 10N aqueous potassium hydroxide solution in a nitrogen atmosphere and the mixture was heated at 50° C. for 2.5 hours. This reaction mixture was then extracted with ether and the extract was dried over magnesium sulfate and concentrated under reduced pressure to give 14.1 g of 2-methylene-1,3,3-trimethylindoline (Yield 81%).

$^1$H-NMR (CDCl$_3$): δppm 1.3 (s, 6H, CH$_3$), 3.0 (s, 3H, N—CH$_3$), 6.5–7.0 (dd, 2H, vinyl), 7.0–7.2 (m, 4H, ArH)

EXAMPLE 7

In 120 ml of 2-butanone were dissolved 14.1 g of 3-methacryloxymethyl-5-nitrothiosalicylaldehyde and 8.7 g of 2-methylene-1,3,3-trimethylindoline and the mixture was refluxed in a nitrogen atmosphere for 20 hours. The reaction mixture was then concentrated under reduced pressure and the residue was purified by silica gel column chromatography to give 15.9 g of 8-methacryloxymethyl-6-nitro-1',3',3'-trimethylspiro[2H-1-benzothiopyran-2,2'-indoline] as light yellow crystals (Yield 73%).

$^1$H-NMR (CDCl$_3$): δppm 1.24 (s, 3H, CH$_3$), 1.39 (s, 3H, CH$_3$), 1.97 (d, 3H, CH$_3$), 2.67 (s, 3H, N—CH$_3$), 5.15 (dd, 2H, CH$_2$), 5.62 (t, 1H, vinyl), 6.05 (d, 1H, thiopyran), 6.16 (s, 1H, vinyl), 6.51 (d, 1H, thiopyran), 6.65 (t, 1H, indoline), 6.96 (d, 1H, indoline), 7.06 (d, 1H, indoline), 7.17 (t, 1H, indoline), 8.02 (d, 1H, benzothiopyran), 8.08 (d, 1H, benzothiopyran)

EXAMPLE 8

In 34 ml of hexane was dissolved 201.2 mg (0.461 mmol) of the 8'-methacryloxymethyl-1,3,3-trimethyl-6'-nitro[(2'H)-1'-benzothiopyran-2,2'-indoline] obtained in Example 7 with heating and the solution was cooled to room temperature to give a yellow clear solution. When this solution was irradiated with ultraviolet light using a 500 W super-high-pressure mercury vapor lamp fitted with a band pass filter adapted to transmit light of the wavelength of about 350 nm at room temperature for 5 hours, microfine red crystals separated out. The crystals were recovered by filtration and dried under reduced pressure to give 110 mg of red crystals (Yield 55%). m.p. 123°–124° C.

The $^1$H-NMR spectrum of this crystalline produce at $-40°$ C. showed not only the signals characteristic of the above starting compound but also the following signals assignable to the ring opened isomer (of the following structural formula) with substantially the same intensity.

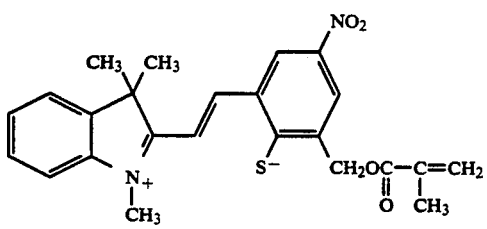

(δppm: 1.85 (s, 6H), 1.87 (s, 3H), 4.26 (s, 3H), 5.34 (s, 2H), 5.60 (s, 1H), 6.26 (s, 1H), 7.64 (m, 2H), 7.85 (m, 4H), 8.60 (s, 1H), 9.73 (d, 1H))

It was, thus, confirmed that the red crystalline product was a substantially equimolar mixture of the starting compound and its ring opened isomer. The elemental analysis of the crystal, C:65.88%, H:5.38% and N:6.16%, was in agreement with that of the starting compound within the margin of error.

When the above red microfine crystals were spread uniformly on a strip of filter paper and pressed with a plastic spoon under finger pressure, they developed a brilliant deep blue color.

The compound thus pressed to produce a deep blue color was dissolved in hexane with heating and the above procedure was repeated. In this manner, it could be reconverted to piezochromic red crystals and reused.

EXAMPLE 9

In 3 ml of chloroform were dissolved 1.59 g of 2,3,3-trimethylindolenine and 2.57 g of 2-iodoethanol and the solution was stirred in a sealed tube at 120° C. for 20 hours. The resulting blackish brown oil was dissolved in acetone-methanol followed by addition of ether and the crystals thus obtained were recovered by filtration. In this manner, 2.65 g of N-hydroxyethylindolenium iodide was obtained (Yield 80%).

$^1$H-NMR (CDCl$_3$): δppm 1.53 (s, 6H, CH$_3$), 2.80 (s, 3H, CH$_3$), 3.86 (t, 2H, CH$_2$), 4.57 (t, 2H, CH$_2$), 7.65 (dd, 2H, ArH), 7.83 (dd, 1H, ArH), 7.93 (dd, 1H, ArH)

EXAMPLE 10

In 35 ml of ethanol was dissolved 1.07 g of hydroxyethylindolenium iodide followed by addition of 0.59 g of 5-nitrothiosalicylaldehyde dissolved in 5 ml of 2-butanone and the mixture was stirred at room temperature. To this was added a solution of 0.36 g of triethylamine in 6 ml of ethanol and the mixture was heated and reacted under reflux for 1.5 hours. The reaction mixture was then concentrated and the blackish brown residue was purified by silica gel column chromatography to give 0.63 g of 1-hydroxyethyl 6'-nitro-3,3-dimethylspiro[2'H-1-benzothiopyran-2,2'-indoline] as yellow crystals (Yield 56.8%).

$^1$H-NMR (CDCl$_3$): δppm 1.26 (s, 3H, CH$_3$), 1.41 (s, 3H, CH$_3$), 1.73 (t, 1H, OH), 3.19 (m, 1H, CH$_2$), 3.46 (m, 1H, CH$_2$), 3.80 (m, 2H, CH₂), 6.03 (d, 1H, vinyl), 6.59 (d, 1H, ArH), 6.87 (d, 1H, vinyl), 6.89 (t, 1H), 7.09–8.02 (m, 5H)

EXAMPLE 11

In 4 ml of dichloromethane was dissolved 0.40 g of 1-hydroxyethyl-6'-nitro-3,3-dimethylspiro[2'H-1'-benzothiopyran-2,2'-indoline] followed by addition of 0.18 g of triethylamine to give a homogenous solution. To this was added dropwise a solution of 0.18 g of methacrylic acid chloride in 1 ml of dichloromethane and the mixture was stirred at room temperature for 1.5 hours. The reaction mixture was concentrated and the residue was purified by silica gel column chromatography to give 0.40 g of 1-methacryloxyethyl-6'-nitro-3,3-dimethylspiro[2'H-1'-benzothiopyran-2,2'-indoline] as yellow crystals (Yield 79.1%).

¹H-NMR (CDCl₃): δppm
1.21 (s, 3H, CH₃), 1.39 (s, 3H, CH₃), 1.94 (s, 3H, CH₃), 3.32 (m, 1H, CH₂), 3.61 (m, 1H, CH₂), 4.34 (m, 2H, CH₂), 5.59 (m, 1H, vinyl), 6.01 (d, 1H, thiopyran), 6.11 (m, 1H, vinyl), 6.63 (d, 1H), 6.87 (d, 1H), 6.88 (t, 1H), 7.08–8.02 (m, 5H)

EXAMPLE 12

In 35 ml of hexane was dissolved thoroughly 225 mg of the 1-methacryloxyethyl-6'-nitro-3,3-dimethylspiro[2'H-1'-benzothiopyran-2,2'-indoline] with heating, whereupon a light yellow clear solution was obtained. When this solution was irradiated with ultraviolet light with a 500 W super-high-pressure mercury vapor lamp fitted with a band pass filter adapted to transmit light of the wavelength of about 350 nm at room temperature for 3 hours, reddish orange-colored crystals separated out. These crystals were recovered by filtration and dried. In this manner, 123 mg of reddish orange-colored crystals were obtained (Yield 54%).

m.p. 94°–98° C.

The crystals were dissolved in deuterochloroform at −40° C. and the ¹H-NMR spectrum was determined at the same temperature. The spectrum showed not only the signals of the starting compound but also the following signals assignable to its ring opened isomer (of the following structural formula) with approximating ⅔ intensities as follows.

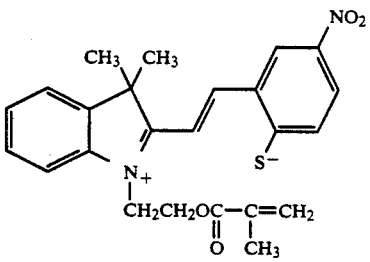

(δppm: 1.55 (bs, 6H, CH₃), 1.91 (s, 3H, CH₃), 4.40 (m, 2H, CH₂), 4.65 (m, 2H, CH₂), 5.55 (s, 1H, vinyl), 6.24 (s, 1H, vinyl), 7.14–7.96 (m, 6H), 8.01 (s, 1H), 8.54 (d, 1H), 9.52 (d, 1H))

The solution just after NMR spectrophotometry was green but when allowed to stand at room temperature, it became light yellow and clear. The ¹H-NMR spectrum of the solution after fading was different from that of the green solution and in complete agreement with that of the starting compound.

Based on the above results, the reddish orange-colored crystal was confirmed to be a 60:40 mixture of the starting compound and its ring opened isomer. The elemental analysis of the crystal, C:65.81%, H:5.36% and N:6.20%, was in agreement with that of the starting compound within the margin of error.

EXAMPLE 13

To a solution of 1.6 g of 2,3,3-trimethylindolenine in 10 ml of chloroform was added 2.8 g of 1-bromodecane and the mixture was heated in an autoclave at 80° C. for 20 hours. The resulting precipitate was recovered by filtration to give 3.7 g of 1-dodecyl-2,3,3-trimethylindolenium as white crystals. To the crystals was added 40 ml of 10N aqueous potassium hydroxide solution and the mixture was heated at 50° C. for 3 hours. The reaction mixture was then extracted with ether and the extract was dried over magnesium sulfate and concentrated under reduced pressure to give 2.7 g of 3,3-dimethyl-1-dodecyl-2-methyleneindoline (Yield 82%).

¹H-NMR (CDCl₃): δppm
0.87 (t, 3H), 1.25 (s, 18H), 1.30 (s, 6H), 1.62 (m, 2H), 3.03 (m, 2H), 6.60 (dd, 2H), 7.6–8.0 (m, 4H)

EXAMPLE 14

In 6 ml of 2-butanone were dissolved 2.7 g of 3,3-dimethyl-1-dodecyl-2-methyleneindoline and 1.7 g of 5-nitrothiosalicylaldehyde and the mixture was refluxed in a nitrogen atmosphere for 20 hours. The reaction mixture was then concentrated under reduced pressure and the residue was purified by silica gel column chromatography to give 3.0 g of 3,3-dimethyl-1-dodecyl-6'-nitrospiro[2'H-1'-benzothiopyran-2,2'-indoline] as light yellow crystals (Yield 72.7%).

¹H-NMR (CDCl₃): δppm
0.88 (t, 3H), 1.21 (s, 3H), 1.26 (s, 18H), 1.40 (s, 3H), 1.63 (m, 2H), 3.0–3.25 (m, 2H), 6.02 (d, 1H), 6.45 (d, 1H), 6.79–7.09 (m, 3H), 7.40–7.62 (m, 2H), 7.92–8.13 (m, 2H)

EXAMPLE 15

Using 240 mg of the 3,3-dimethyl-1-dodecyl-6'-nitrospiro[2'H-1'-benzothiopyran-2,2'-indoline] obtained in Example 14, ultraviolet irradiation and aftertreatment were carried out as in Example 12. In this manner, 92 mg of reddish orange-colored crystals were obtained (Yield 38%).

m.p. 85°–88° C.

The ¹H-NMR spectrum of this crystalline product was determined as in Example 12. The spectrum showed not only the signals of the starting compound but also the following signals assignable to its ring opened isomer (of the following structural formula) with about ⅔ intensities.

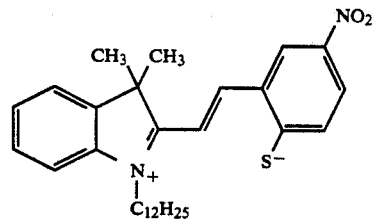

(δppm: 0.89 (t, 3H, CH₃), 1.24 (s, 18H, CH₂), 1.52 (s, 6H, CH₃), 1.70 (s, 2H, CH₂), 4.48 (m, 2H, CH₂), 7.31–7.91 (7H), 8.50 (m, 1H), 9.61 (d, 1H))

The solution just after NMR spectrophotometry was green but when allowed to stand at room temperature, it became light yellow and clear. The ¹H-NMR spectrum after fading was different from that of the previous green solution and in complete agreement with that of the starting compound.

Based on the above results, the reddish orange-colored crystal was confirmed to be an approximately 60:40 mixture of the starting compound and its ring opened isomer. The elemental analysis of this crystal, C:72.99%, H:8.20% and N:5.56%, is in complete agreement with that of the starting compound within the margin of error.

EXAMPLE 16

To a solution of 4.0 g of 2,3,3-trimethylindolenine in 25 ml of chloroform was added 5.6 g of p-methoxybenzyl bromide and the mixture was heated in an autoclave at 80° C. for 21 hours. The resulting precipitate was recovered by filtration to give 8.5 g of 1-(4-methoxybenzyl)-2,3,3-trimethylindolenium as white crystals. To these crystals was added 85 ml of 10N aqueous potassium hydroxide solution in a nitrogen atmosphere and the mixture was heated at 50° C. for 3 hours. The reaction mixture was then extracted with ether and the extract was dried over magnesium sulfate and concentrated under reduced pressure to give 5.7 g of 3,3-dimethyl-1-(4-methoxybenzyl)-2-methyleneindoline (Yield 80.6%).

¹H-NMR (CDCl₃): δppm 1.31 (s, 6H), 3.48 (s, 3H), 4.82 (s, 2H), 6.5–6.8 (dd, 2H), 7.0–7.8 (8H)

EXAMPLE 17

In 15 ml of 2-butanone were dissolved 5.7 g of 3,3-dimethyl-1-(4-methoxybenzyl)-2-methyleneindoline and 4.1 g of 5-nitrothiosalicylaldehyde and the mixture was refluxed in a nitrogen atmosphere for 22 hours. The reaction mixture was then concentrated under reduced pressure and the residue was purified by silica gel column chromatography to give 6.2 g of 3,3-dimethyl-1-(4-methoxybenzyl)-6'-nitrospiro[2'H-1'-benzothiopyran-2,2'-indoline] as light yellow crystals (Yield 68.4%)

¹H-NMR (CDCl₃): δppm 1.25 (s, 3H), 1.40 (s, 3H), 3.80 (s, 3H), 4.44 (s, 2H), 6.05 (d, 1H), 6.50 (d, 1H), 6.7–8.3 (m, 11H)

EXAMPLE 18

Using 205 mg of the 3,3-dimethyl-1-(4-methoxybenzyl)-6'-nitrospiro[2'H-1'-benzothiopyran-2,2'-indoline] obtained in Example 17, ultraviolet irradiation and after-treatment were carried out as in Example 12 to give 126 mg of reddish orange-colored crystals (Yield 61%). m.p. 111°–115° C.

The ¹H-NMR spectrum of this crystalline product was determined as in Example 12. The spectrum revealed not only the signals of the starting compound but also the following signals assignable to its ring opened isomer (of the following structural formula) with approximately ⅔ intensities.

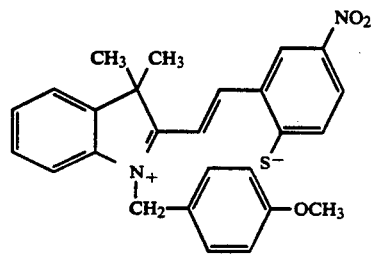

(δppm: 1.62 (s, 6H, CH₃), 3.72 (s, 3H, CH₃O), 5.58 (s, 2H, CH₂), 6.9–8.5 (m, 11H), 8.60 (m, 1H), 9.65 (d, 1H))

The solution just after NMR spectrophotometry was green but, when allowed to stand at room temperature, underwent gradual fading to become light yellow and clear. The ¹H-NMR spectrum after fading was different from that of the previous solution and in complete agreement with that of the starting compound.

It was, therefore, clear that the reddish orange-colored crystalline product was an approximately 60:40 mixture of the starting compound and its ring opened isomer. Its elemental analysis, C:70.45%, H:5.23% and N:6.35%, was in agreement with that of the standard compound within the margin of error.

EXAMPLE 19

Using 200 mg of 1,3,3-trimethyl-6'-nitro[2'H-1'-benzothiopyran-2,2'-indoline], ultraviolet irradiation and after-treatment were carried out in the same manner as Example 12. As a result, 140 mg of the object product was obtained as reddish orange-colored crystals (Yield 70%).

The ¹H-NMR spectrum of this crystalline product, determined in the same manner as Example 12, revealed not only the signals of the starting compound but also the following signals assignable to its ring opened isomer (of the following structured formula).

(δppm: 1.60 (s, 6H, CH₃), 4.20 (s, 3H, CH₃N), 7.40–7.80 (5H), 7.82 (d, 1H), 7.99 (s, 1H), 8.70 (s, 1H), 9.58 (d, 1H))

The solution just after NMR spectrophotometry was green but, when allowed to stand at room temperature, under went gradual fading to become light yellow and clear. The ¹H-NMR spectrum determined after fading was different from that of the previous green solution and was in complete agreement with that of the starting compound.

These results indicated that the reddish orange-colored crystalline product was an approximately equimolar mixture of the starting compound and its ring opened isomer. Its elemental analysis of C:67.33%, H:5.29% and N:8.11% was in agreement with that of the starting compound within the margin of error.

EXAMPLE 20

Using a soft brush, the microfine red crystals obtained in Example 8 were spread uniformly in an ultrathin layer on a silica gel plate consisting of an aluminum base plate and a 0.2 mm thick layer of silica gel as bonded thereto (Merck, Art. 5554). Then, collodion was coated in superimposition on the crystal layer and dried to provide an orange-colored piezochromic plate. This plate became brilliant deep blue on mere rubbing of its surface with a plastic spatula. When exposed to visible light, the blue area faded to give the original orange color and this cycle of color change could be repeated.

Figure 1:
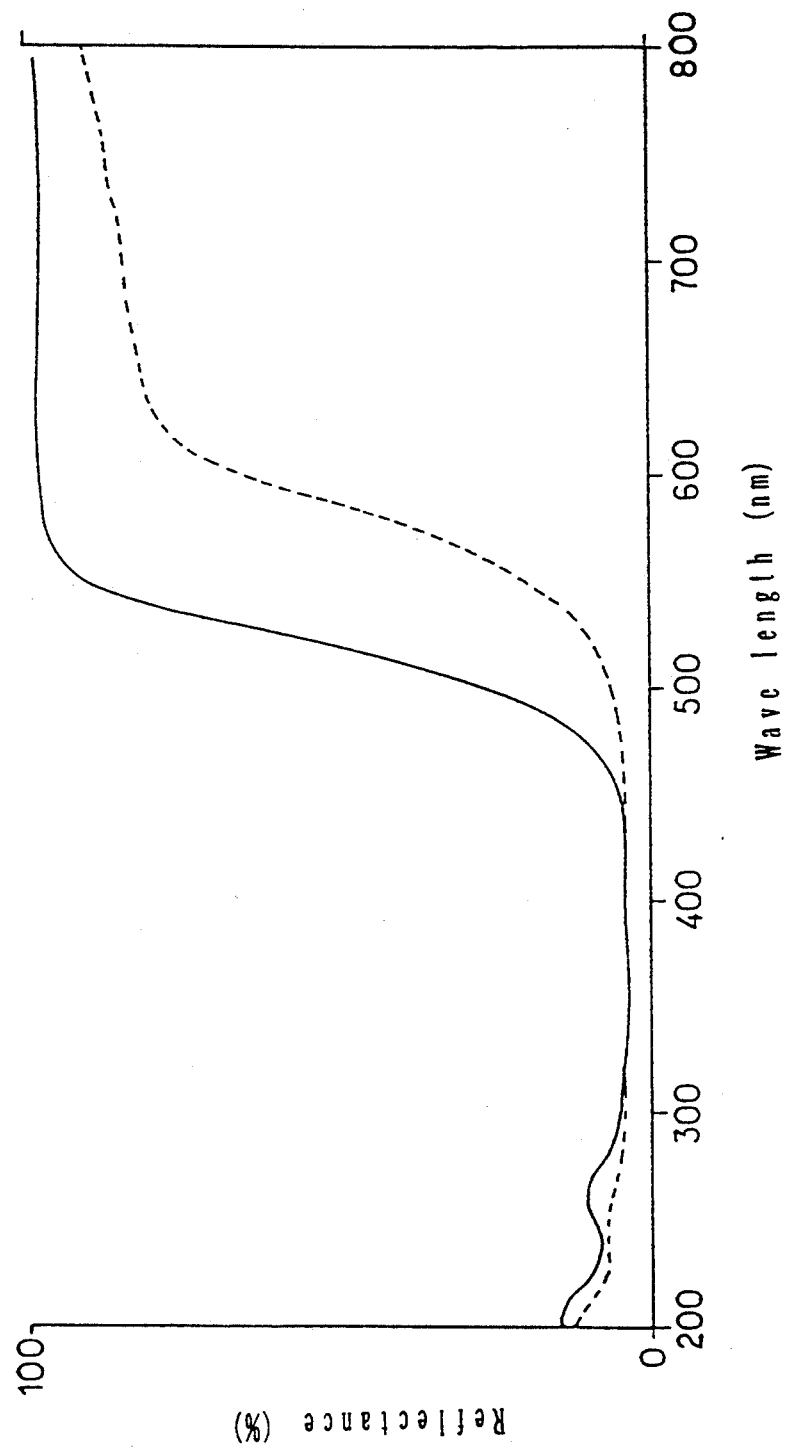
FIG. 1 shows solid UV absorption spectra of the starting compound (1) used and the crystal (2) obtained in Example 8.
Figure 2:
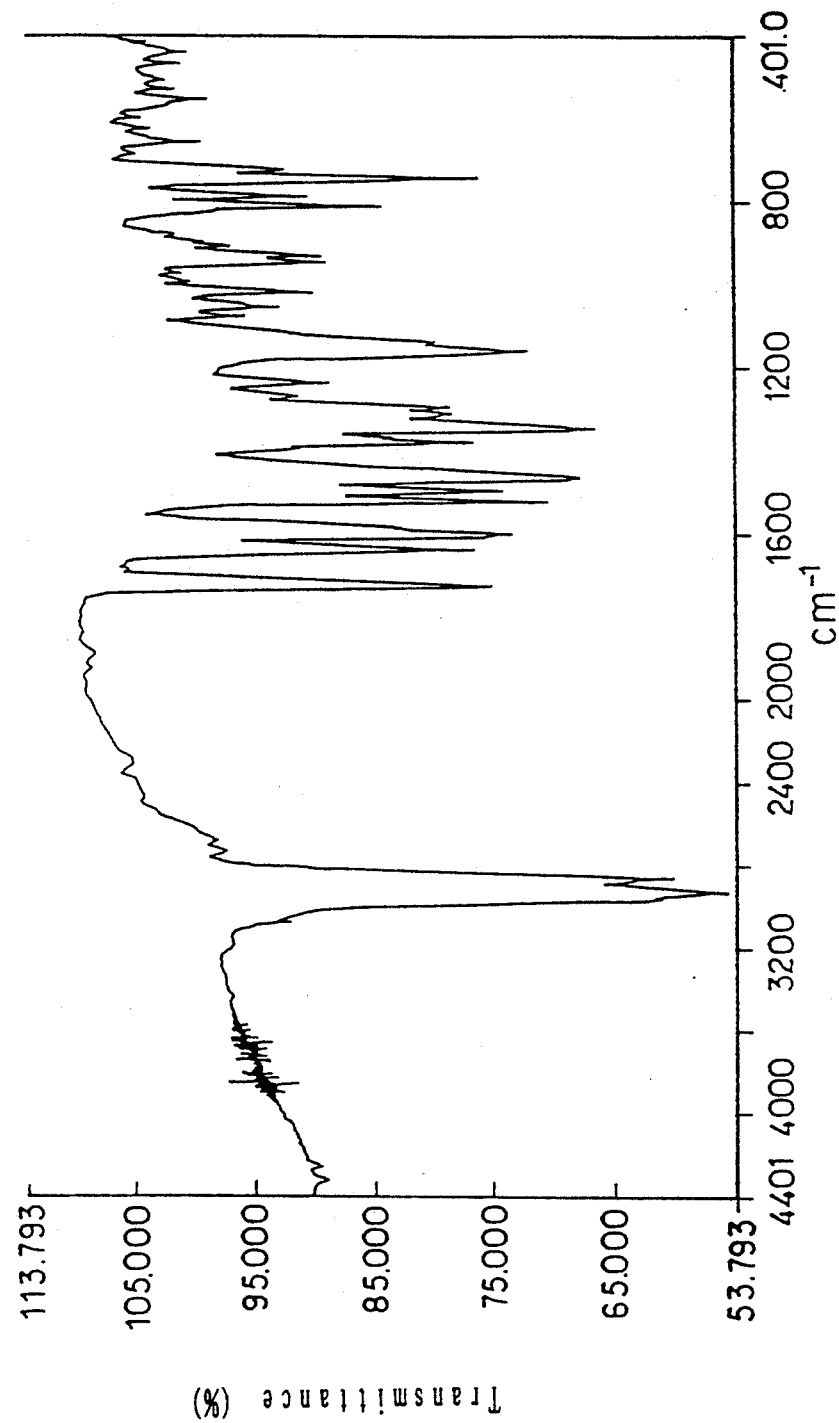
FIG. 2 is an IR spectrum of the crystal obtained in Example 8.

I claim:

1. A crystal comprising an indolinospirobenzothiopyran derivative of the following general formula and its ring opened isomer,

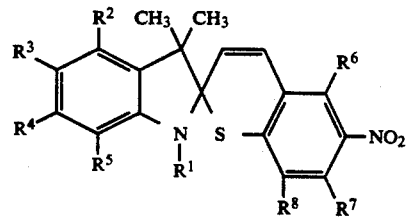

wherein $R^1$ means an alkyl group of 1 to 20 carbon atoms, an aralkyl group, a methacryloxymethyl group or a methacryloxyethyl group, $R^2$, $R^3$, $R^4$ and $R^5$ may be the same or different and each means a hydrogen atom, an alkyl group of 1 to 6 carbon atoms, an aryl group, an aralkyl group, an alkoxy group of 1 to 5 carbon atoms, a halogen atom, a cyano group or a nitro group, $R^6$ and $R^7$ may be the same or different and each means a hydrogen atom, an alkyl group of 1 to 6 carbon atoms, an aryl group, an aralkyl group, a halogen atom, a cyano group or a nitro group, $R^8$ means a hydrogen atom, an alkyl group of 1 to 6 carbon atoms, an alkoxy group of 1 to 5 carbon atoms, a chloromethyl group, a methacryloxymethyl group or a vinyl group.

2. The crystal of claim 1 which comprises 30 to 60 mol % of the indolinospirobenzothiopyran derivative and 70 to 40 mol % of its ring opened isomer as claimed in claim 1.

3. A process for producing the crystal of claim 1 or 2 which is characterized by dissolving the indolinospirobenzothiopyran derivative of claim 1 in a low-polarity organic solvent and irradiating the same with ultraviolet light.

4. The process of claim 3 wherein said organic solvent is a nonpolar solvent.

5. A piezochromic material comprising the crystal of claim 1.

* * * * *